United States Patent
McCartan et al.

(10) Patent No.: US 6,270,460 B1
(45) Date of Patent: Aug. 7, 2001

(54) APPARATUS AND METHOD TO LIMIT THE LIFE SPAN OF A DIAGNOSTIC MEDICAL ULTRASOUND PROBE

(75) Inventors: Dermot McCartan, Sunnyvale; Gregory A. Reynolds, Saratoga; John D. Marshall, Redwood City, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/344,313

(22) Filed: Jun. 24, 1999

(51) Int. Cl.[7] .................................................... A61B 8/12
(52) U.S. Cl. ............................................................. 600/459
(58) Field of Search ................................... 600/437, 443, 600/447, 459; 73/618, 620–621

(56) References Cited

U.S. PATENT DOCUMENTS

| | | | |
|---|---|---|---|
| 4,868,476 | 9/1989 | Respaut | 318/632 |
| 5,487,386 | 1/1996 | Wakabayashi et al. | 660/447 |
| 5,731,716 | 3/1998 | Pascucci | 326/106 |
| 5,804,162 | * 9/1998 | Kabalnov et al. | 424/951 |
| 6,029,083 | 2/2000 | Flower et al. | 604/20 |

* cited by examiner

Primary Examiner—Marvin M. Lateef
Assistant Examiner—Ali M. Imam
(74) Attorney, Agent, or Firm—Brinks Hofer Gilson & Lione

(57) ABSTRACT

An ultrasound probe for diagnostic medical ultrasound imaging, including an ultrasound transducer and a circuit having a plurality of states to limit the use of the ultrasound probe. Ultrasound probe use can be limited based on a unique identification number (e.g., selected by means of electrically programmable fuses) assigned to each ultrasound probe. Alternatively, the ultrasound system software monitors and updates the number of times that the ultrasound probe has been used. Another aspect of the invention is directed to an ultrasound system, including an ultrasound probe with multiple states, a circuit to program and to receive state data from the ultrasound probe and interpret the state data, and a cable to communicate state data between the ultrasound probe and the processor. Another aspect of the invention is directed to a method for using a limited use ultrasound probe, including the steps of determining the state of a circuit in the limited use ultrasound probe and determining if the ultrasound probe can be used.

19 Claims, 8 Drawing Sheets

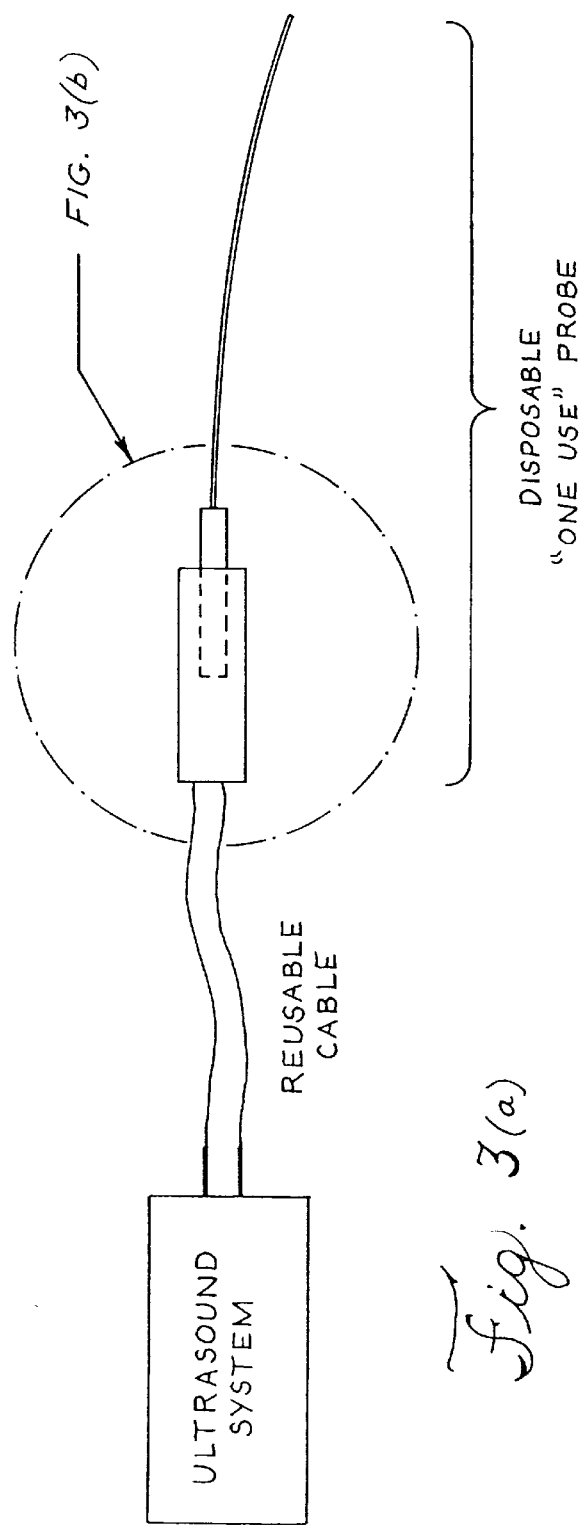
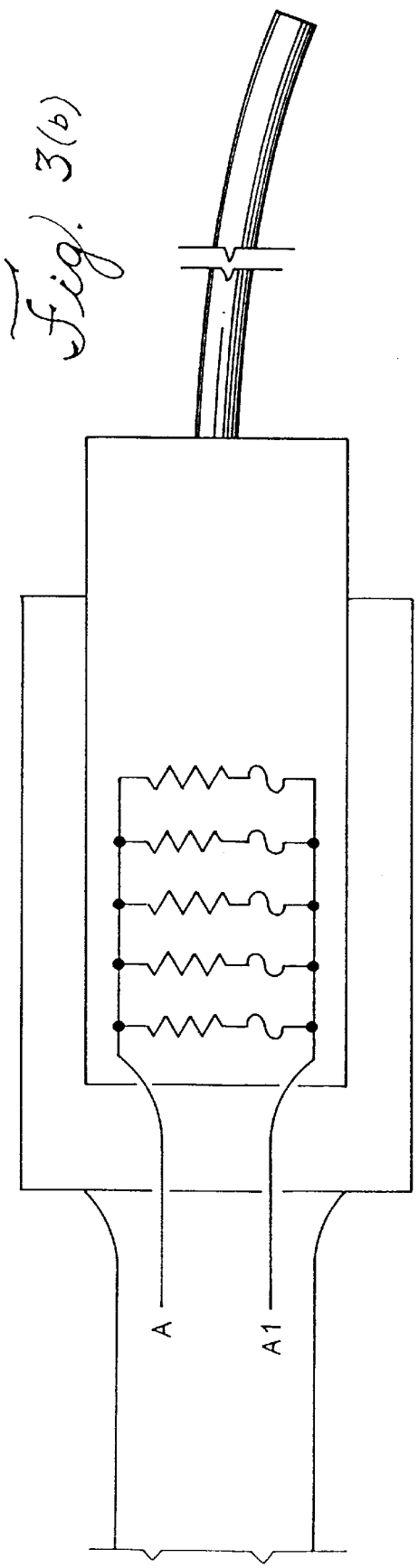

| FUSE BLOWN | VA, A¹ | RSENSE |
|---|---|---|
| F1 | 1.25 v | 13.53 Ω |
| F1, F2 | 2.50 v | 28.57 Ω |
| F1 - F3 | 5.0 v | 66.67 Ω |
| F1 - F4 | 10.0 v | 200 Ω |
| F1 - F5 | 20.0 v | OPEN |
| (NONE) | — | 6.42 Ω |

# APPARATUS AND METHOD TO LIMIT THE LIFE SPAN OF A DIAGNOSTIC MEDICAL ULTRASOUND PROBE

BACKGROUND OF THE INVENTION

1. Field of the Invention

This invention relates generally to an improvement in diagnostic medical ultrasound imaging, and more specifically to an improved system, method, and ultrasound probe for limiting the usage of the ultrasound probe, after a predetermined time of usage or number of usages of the ultrasound probe.

2. Description of the Prior Art

There is growing interest in ultrasound systems for medical applications. Commonly available ultrasound systems for medical applications normally use ultrasound probes with a one-dimensional (1-D), 1.5-D, or 2-D ultrasound transducer array for obtaining images.

Major applications for imaging with diagnostic medical ultrasound frequently require the insertion of an ultrasound probe into a human body for improved imaging. Therefore, some medical ultrasound probes are designed for only one use. This is because the ultrasound probes come into contact with bodily fluids, such as blood, saliva or bile. Re-use of the ultrasound probe carries the possible risk of cross contamination between patients, i.e., HIV, various types of hepatitis, and other diseases spread by bodily fluid contact.

Because these ultrasound probes are designed for only one use, each ultrasound probe must be relatively inexpensive in manufacturing and materials cost for medical cost-effectiveness. Therefore, these ultrasound probes do not generally have the rugged construction of the more expensive re-usable ultrasound probes.

These ultrasound probes are designed to be delivered to the customer pre-sterilized and tested. Therefore, the ultrasound probe materials are chosen to be suitable for a specific form of factory sterilization. This means the materials used may not be suitable for other sterilization techniques commonly used in hospitals, such as radiation, various chemical treatments, etc. If an ultrasound probe is subjected to a sterilization technique for which it was not designed, the ultrasound probe may degrade, e.g., a leakage current fault may occur, or a breakdown may occur in one of the insulating sleeves. If such an ultrasound probe is re-used, patient safety is severely compromised. And if a fault should occur in the ultrasound probe due to improper sterilization techniques, it is not easy to verify the electrical integrity of the ultrasound probe. Because the ultrasound probe is designed for one time use only, the ultrasound probe manufacturer normally supplies no means to enable customer verification of the electrical integrity of the ultrasound probe.

Therefore, misuse of an ultrasound probe can be dangerous to patients and an ultrasound probe manufacturer is legally liable in many jurisdictions for the foreseeable, abnormally dangerous misuse of an ultrasound probe. Therefore, there is a need for an improved system, method, and ultrasound probe to limit the life span of the ultrasound probe. What is also needed is a low cost system and method for identifying an ultrasound probe, for indicating the number of times the ultrasound probe has been used, or for indicating the amount of time the ultrasound probe has been in use.

SUMMARY OF THE INVENTION

One object of the present invention is to provide a system, method, and ultrasound probe to limit the life span of the ultrasound probe.

Another object of the invention is to provide a low cost system and method for identifying an ultrasound probe, for indicating the number of times the ultrasound probe has been used, or for indicating the amount of time the ultrasound probe has been in use.

A first aspect of the invention is directed to an ultrasound probe that includes an ultrasound transducer and a circuit having a plurality of states to limit the use of the ultrasound probe.

A second aspect of the invention is directed to an ultrasound system that includes an ultrasound probe with a plurality of states, a circuit to program the states of the ultrasound probe and receive state data from the ultrasound probe and interpret the state data, and a cable to communicate state data between the ultrasound probe and the circuit.

A third aspect of the invention is directed to a method for using a limited use ultrasound probe, including the steps of determining the state of a circuit in the limited use ultrasound probe and determining if the ultrasound probe can be used.

These and other objects and advantages of the invention will become apparent to those skilled in the art from the following detailed description of the invention and the accompanying drawings.

BRIEF DESCRIPTION OF THE DRAWINGS

FIG. 3(a) is a schematic diagram of an ultrasound system, a re-usable cable, and a disposable "one-use" ultrasound probe connected by the re-usable cable to the ultrasound system.

FIG. 3(b) is an enlarged schematic diagram showing a fuse and resistor circuit, according to one embodiment of the invention, of the disposable ultrasound probe shown in FIG. 3(a).

DETAILED DESCRIPTION OF PREFERRED EMBODIMENTS OF THE INVENTION

Figure 1A:
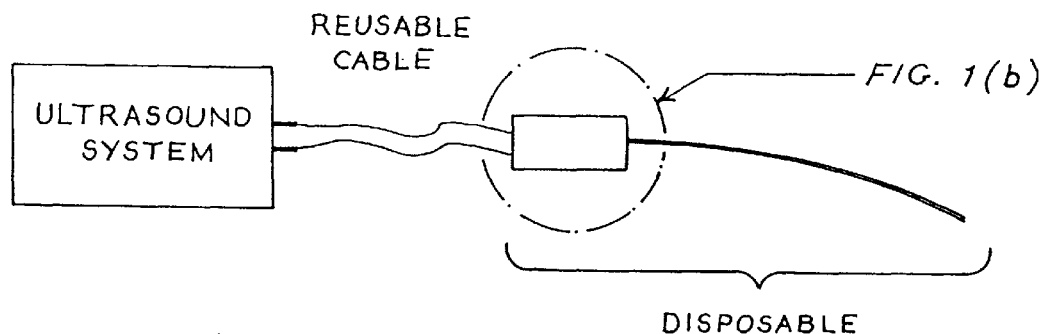
FIG. 1(a) is a schematic diagram of an ultrasound system, a re-usable cable, and a disposable ultrasound probe connected by the re-usable cable to the ultrasound system.

The invention helps solve the problems discussed above by limiting the life span of the ultrasound probe. This can be accomplished in a number of ways, either via software or hardware, or a combination thereof. In preferred embodiments of the invention, an ultrasound system prevents further imaging with the ultrasound probe, after a predetermined time of usage or number of usages of the ultrasound probe. Subsequent usage of an "expired" ultrasound probe is also prevented by the invention.

Several techniques could be used to disable an ultrasound probe connected to an ultrasound system to prevent further imaging. One technique is to activate software or hardware in the ultrasound system that pulls a reset line down to halt imaging, if imaging with the ultrasound probe is not allowed by the ultrasound system. Another technique is to mimic or initiate a fault (e.g., a thermal fault), which will prevent further imaging with the ultrasound probe. Another technique is to incorporate software in the ultrasound system to control and monitor an enable line that must be enabled before ultrasound probe imaging can occur.

In embodiments of the invention that allow an ultrasound probe to be used multiple times, it is necessary to manufacture the ultrasound probe more ruggedly, so that it can withstand multiple sterilizations and multiple usage. However, this increases the cost of the ultrasound probe.

In one preferred embodiment of the invention, each ultrasound probe is serialized by embedding a unique identification number (ID), for example, by means of electrically programmable fuses or non-volatile digital memory (i.e., the memory contents are not lost if power is removed). The ID is readable by an ultrasound system, preferably by software, but alternatively, by hardware. The ultrasound system, via software, transmits the ID number, along with the amount of time the ultrasound probe has been in use, to a memory inside the ultrasound system. After a predetermined length of time has passed, the ultrasound system does not allow further imaging with the ultrasound probe. Each time an ultrasound probe is connected to the ultrasound system, the system checks the ultrasound probe's ID and compares it with previous ultrasound probe IDs in memory. If the ultrasound probe ID is a new ID or there is time remaining for ultrasound probe operation, the ultrasound system allows the ultrasound probe to be used. If the ultrasound probe has already been used for the time limit, no further usage is permitted.

In preferred embodiments of the invention, N fusible links are built into the disposable ultrasound probe. These links can be fabricated from simple wire links, or from actual fuses. Each time the ultrasound probe is attached to the ultrasound system, the ultrasound system checks the status of the fusible links. If all the links are open-circuited, the ultrasound system will not allow the ultrasound probe to be used. On the other hand, if the ultrasound probe has some or all of the fuse links intact, the system acknowledges the ultrasound probe and allows it to be used.

In another preferred embodiment of the invention, the ultrasound system will systematically 'blow' another link after each x minutes of ultrasound probe usage time. This continues until all the links are open-circuited. At this point, if the ultrasound probe is being used in a medical procedure, the ultrasound system could allow imaging to continue until the medical procedure is finished, the ultrasound probe is removed, or the ultrasound probe power is cycled. Any subsequent ultrasound probe usage is not allowed as described previously.

Electrically programmable fuses are commercially available from Cooper Bussmann, Inc., located in St. Louis, Mo., and Wickmann USA, Inc., located in Atlanta, Ga. Nonvolatile digital memory, such as electrically erasable programmable read only memory (EEPROM), and non-volatile random access memory (NVRAM or NOVRAM), are commercially available from Xicor, Inc., located in Milpitas, Calif., Catalyst Semiconductor, Inc., located in Sunnyvale, Calif., and Microchip Technology, Inc., located in Chandler, Ariz.

Another embodiment of the invention could use one or more time-elapsed fuses. A time-elapsed fuse, which has a delay time between the time of maximum current flow and the actual opening of the fuse circuit, could prevent imaging with the ultrasound probe a few hours after a fuse is subjected to the current flow intended to open the fuse. This would allow imaging with the ultrasound probe to continue for a limited time during a medical procedure, but would prevent later imaging with the ultrasound probe after the passage of a number of hours. Accordingly, the probe in one embodiment could have an operational state and a disabled state, that is independent of system control. In such cases the time-elapsed fuse could be replaced by some other consumable element, such as a filament, or an equivalent element.

FIG. 1(a) is a schematic diagram of an ultrasound system, a re-usable cable, and a disposable ultrasound probe connected by the re-usable cable to the ultrasound system.

Figure 1B:
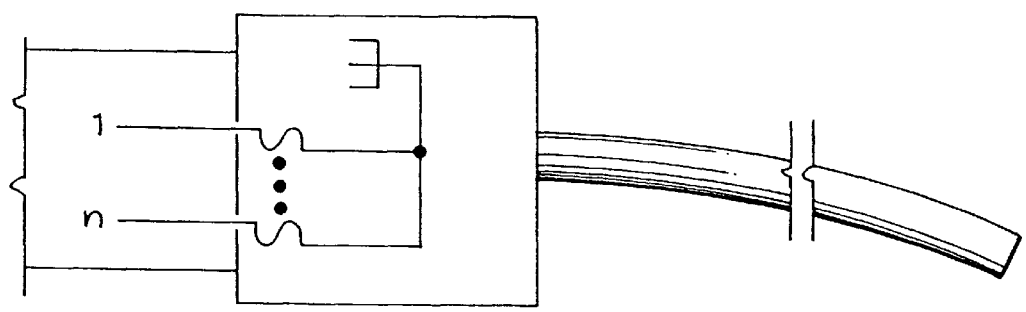
FIG. 1(b) is an enlarged schematic diagram showing a fuse circuit, according to one embodiment of the invention, in the disposable ultrasound probe shown in FIG. 1(a).

FIG. 1(b) is an enlarged schematic diagram showing a fuse circuit, according to one embodiment of the invention, of the disposable ultrasound probe shown in FIG. 1(a).

Figure 1C:
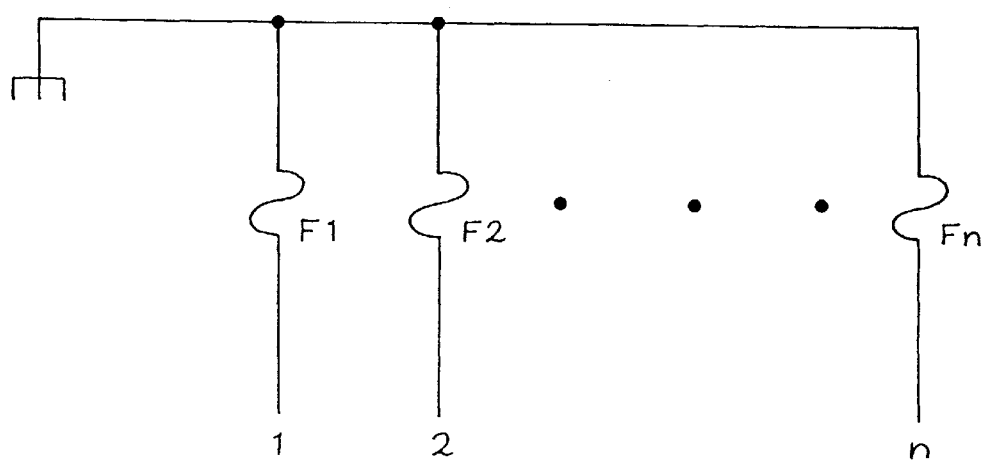
FIG. 1(c) is another enlarged schematic diagram showing the fuse circuit in the disposable ultrasound probe shown in FIG. 1(a).

FIG. 1(c) is another enlarged schematic diagram showing the fuse circuit, according to one embodiment of the invention, of the disposable ultrasound probe shown in FIG. 1(a). FIG. 1(c) shows fuses F1, F2, through FN, all connected to ground and separately connected to N lines.

Figure 2:
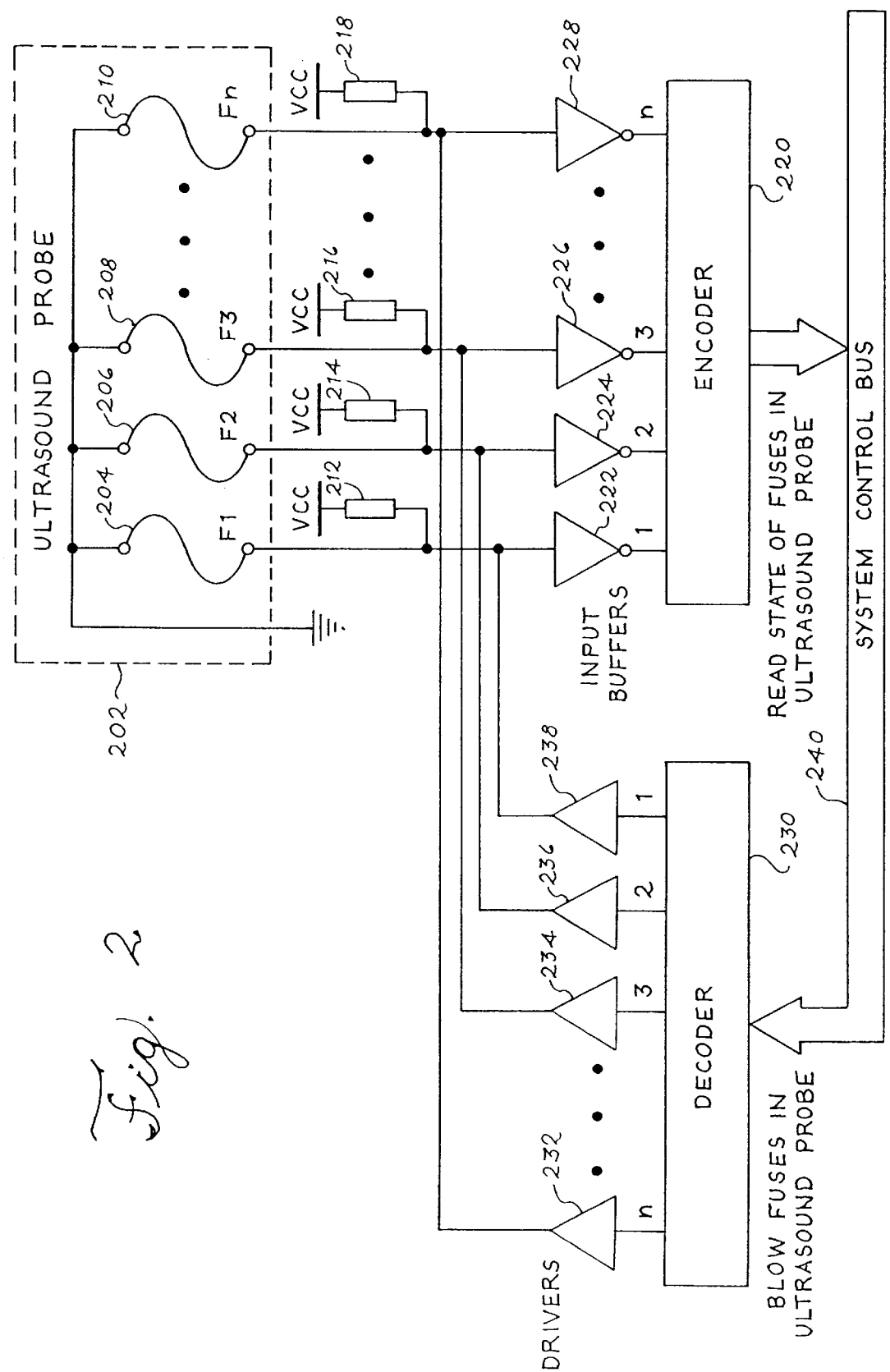
FIG. 2 is a schematic diagram of an ultrasound probe and the encoder, decoder, input buffers, drivers and system control bus for reading and programming the fuses in the ultrasound probe.

FIG. 2 is a schematic diagram of a preferred embodiment of the invention, showing an ultrasound probe 202, encoder 220, decoder 230, input buffers 222, 224, 226, and 228, drivers 232, 234, 236, and 238, and system control bus 240. Ultrasound probe 202 contains fuses F1 204, F2 206, F3 208 through FN 210, which are individually connected through a cable (not shown) to an ultrasound system input port with pull-up resistors 212, 214, 216, and 218 on the input terminals of input buffers 222, 224, 226, and 228. The N bits presented on the input terminals of the input buffers 222, 224, 226, and 228 will be inverted and outputted to the N input terminals of the encoder 220. Encoder 220 will then activate output terminals to communicate the remaining number of uses remaining for the ultrasound probe 202 to system control bus 240. System control bus 240 provides input bits to decoder 230. A bit pattern of N bits output from decoder 230 to the input terminals of drivers 232, 234, 236, and 238 will be transmitted through a cable (not shown) to selectively blow fuses F1 204, F2 206, F3 208 through FN 210. The fuses can selectively be open-circuited for assigning an ID to the ultrasound probe 202 for tracking purposes, or alternatively, for maintaining a record of the number of times of ultrasound probe usage or the time duration of ultrasound probe usage.

Another embodiment of the invention simply blows a single fuse each time the ultrasound probe is initialized, i.e., after N number of initializations occur, all N fuses will be blown. This embodiment of the invention only requires two wires for implementation, one wire for a common ground line and one wire for an I/O line. Each fuse is wired in series with a resistor to form a fuse/resistor pair, then these fuse/resistor pairs are wired in a parallel network. By choosing different values for the resistors, and/or different fuses with different fuse ratings, each individual fuse can be blown separately, depending on the associated resistor value and the input voltage. The status of the fuses can be monitored by applying a smaller voltage to the parallel network and measuring the corresponding current flow.

FIG. 3(a) is a schematic diagram of an ultrasound system, a re-usable cable, and a disposable "one-use" ultrasound probe connected by the re-usable cable to the ultrasound system.

FIG. 3(b) is an enlarged schematic diagram showing a fuse and resistor circuit, according to one embodiment of the invention, of the disposable ultrasound probe shown in FIG. 3(a). Each parallel branch of the circuit has a resistor and a fuse in series.

Figure 4:
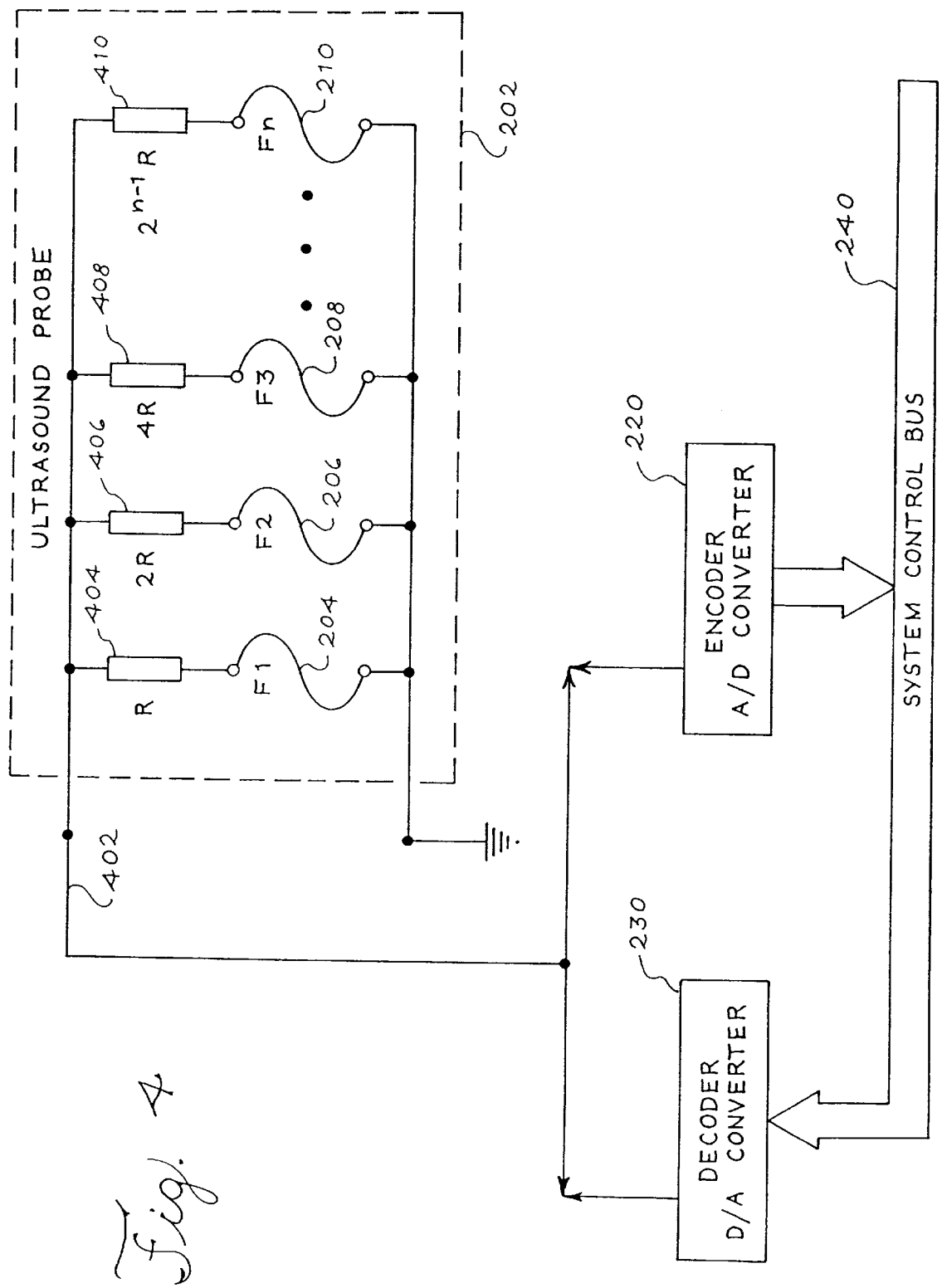
FIG. 4 is a schematic diagram of an ultrasound probe and the encoder, decoder, and system control bus for reading and programming the fuses in the ultrasound probe.

FIG. 4 is a schematic diagram of a preferred embodiment of the invention, showing an ultrasound probe 202, encoder 220, decoder 230, and system control bus 240 for reading and programming the fuses in the ultrasound probe 202. In one preferred embodiment, an analog-to-digital converter performs the functions of encoder 220, and a digital-to-analog converter performs the functions of decoder 230. In another embodiment, an analog circuit performs the functions of encoder 220, and an analog circuit performs the functions of decoder 230. In yet another embodiment, a digital circuit performs the functions of encoder 220, and a digital circuit performs the functions of decoder 230. Ultrasound probe 202 contains an ultrasound transducer (not shown) and fuses F1 204, F2 206, F3 208 through FN 210, which have one terminal connected to a common ground for the ultrasound probe and ultrasound system and one terminal connected to resistors 404, 406, 408, through 410, respectively. These resistors 404, 406, 408, through 410, each have one terminal connected to a common node 402 connected through a cable (not shown) to the input terminals of encoder 220. Encoder 220 will then activate output terminals to communicate the remaining number of uses remaining for the ultrasound probe 202 to system control bus 240. System control bus 240 provides input bits to decoder 230 to selectively blow fuses F1 204, F2 206, F3 208 through FN 210. The fuses F1 204, F2 206, F3 208 through FN 210 can selectively be open-circuited for assigning an ID to the ultrasound probe 202, or alternatively, for maintaining a record of the number of times of ultrasound probe usage or the time duration of ultrasound probe usage.

Figures 5A, 5B:
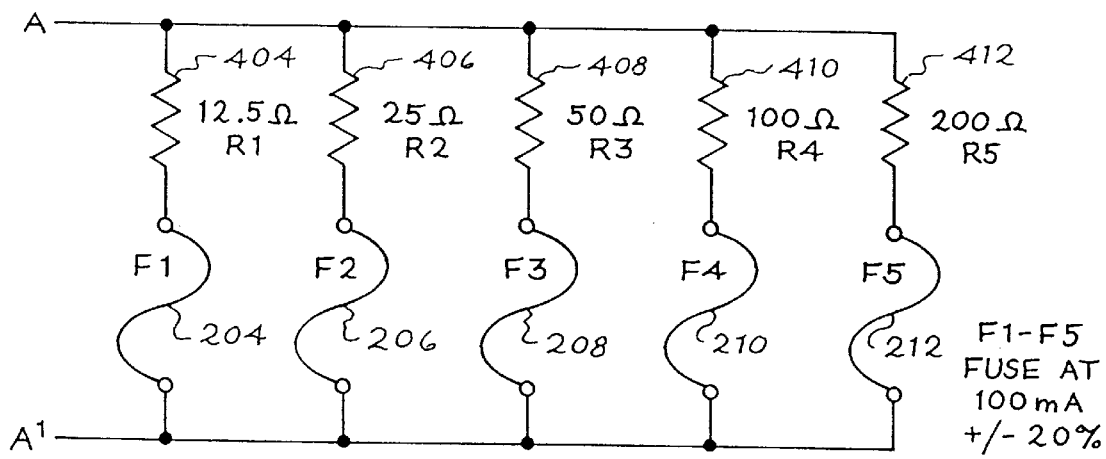
FIG. 5(a) is an enlarged schematic diagram showing a fuse and resistor circuit, according to one embodiment of the invention, of the disposable ultrasound probe shown in FIG. 3(a).
FIG. 5(b) is a table of the measured resistances of the circuit in FIG. 5(a), when various groups of fuses are blown (open-circuited) by applying a voltage to the two terminals of the circuit.

FIG. 5(a) is an enlarged schematic diagram showing a fuse and resistor circuit, according to one preferred embodiment of the invention, of the disposable ultrasound probe shown in FIG. 3(a). The entire parallel circuit has two terminals A and A' for the measurement of resistance of the parallel circuit. Each parallel branch of the circuit has a resistor and a fuse in series. Each fuse F1 204, F2 206, F3 208 through FN 212 can be open-circuited with a current of 100 milli-amperes (mA), within a tolerance of +/−20 mA. The first branch has a fuse F1 204 in series with a resistor R1 404 with a resistance of 12.5 ohms. The second branch has a fuse F2 206 in series with a resistor R2 406 with a resistance of 25 ohms. The third branch has a fuse F3 208 in series with a resistor R3 408 with a resistance of 50 ohms. The fourth branch has a fuse F4 210 in series with a resistor R4 410 with a resistance of 100 ohms. The fifth branch has a fuse F5 212 in series with a resistor R5 412 with a resistance of 200 ohms.

FIG. 5(b) is a table of the measured resistances of the parallel circuit shown in FIG. 5(a), when various groups of fuses are blown (open-circuited) by applying a voltage to the two terminals A and A' of the parallel circuit. When fuse F1 204 is blown by a voltage of 1.25 volts applied across terminals A and A', the measured resistance is 13.53 ohms. When fuses F1 204 and F2 206 are blown by a voltage of 2.5 volts applied across terminals A and A', the measured resistance is 28.57 ohms. When fuses F1 204, F2 206, and F3 208 are blown by a voltage of 5.0 volts applied across terminals A and A', the measured resistance is 66.67 ohms. When fuses F1 204, F2 206, F3 208, and F4 210 are blown by a voltage of 10 volts applied across terminals A and A', the measured resistance is 200 ohms. When fuses F1 204, F2 206, F3 208, F4 210, and F5 212 are blown by a voltage of 20 volts applied across terminals A and A', the measured resistance is infinite, since all the fuses are open-circuited. When none of the fuses are blown, the measured resistance is 6.42 ohms. Therefore, each state of the parallel circuit can be determined by a resistance measurement across terminals A and A'.

Figure 6:
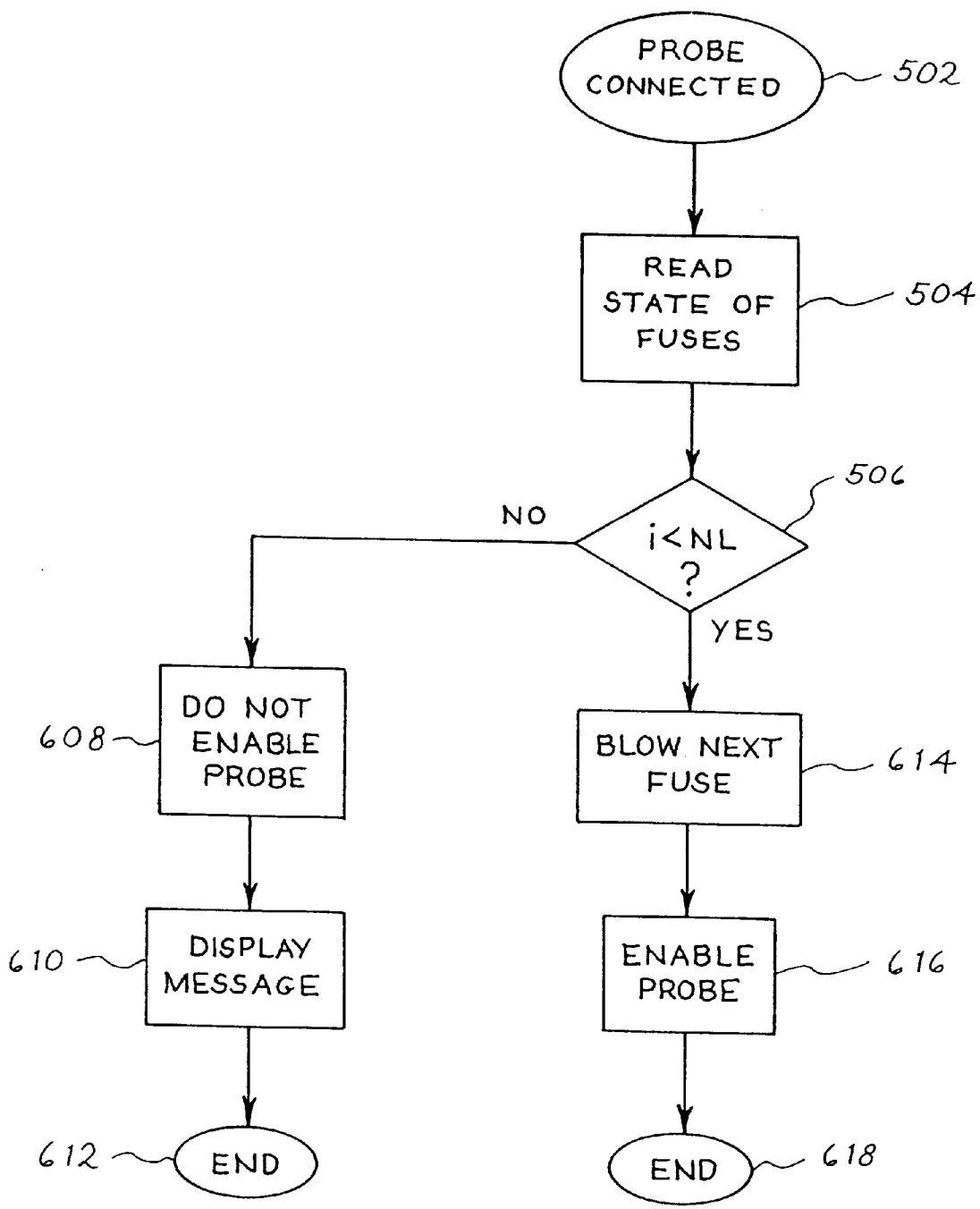
FIG. 6 is a flow chart illustrating an approach for using one embodiment of the invention.

FIG. 6 is a flow chart illustrating a method for using a fuse circuit in one embodiment of the invention. Step 602 involves connecting an ultrasound probe to an ultrasound system. Step 604 involves a processor executing a program in the ultrasound system to read the state of the fuses in the ultrasound probe. Step 606 involves determining whether the ultrasound probe can be used again. If the state of the fuses indicates the maximum amount of ultrasound probe usage has been already reached, then step 608 follows step 606. Step 608 involves disabling the ultrasound probe. Step 610 involves the communication of a message to the user that the ultrasound probe is not available. Step 612 involves ending the ultrasound probe initialization phase of the ultrasound system. If the state of the fuses indicates the maximum amount of ultrasound probe usage has not been already reached, then step 614 follows step 606. Step 614 involves blowing the next fuse in sequence in the ultrasound probe. Step 616 involves enabling the ultrasound probe. Step 618 involves the communication of a message to the user that the ultrasound probe is available and ends the ultrasound probe initialization phase of the ultrasound system.

Figure 7:
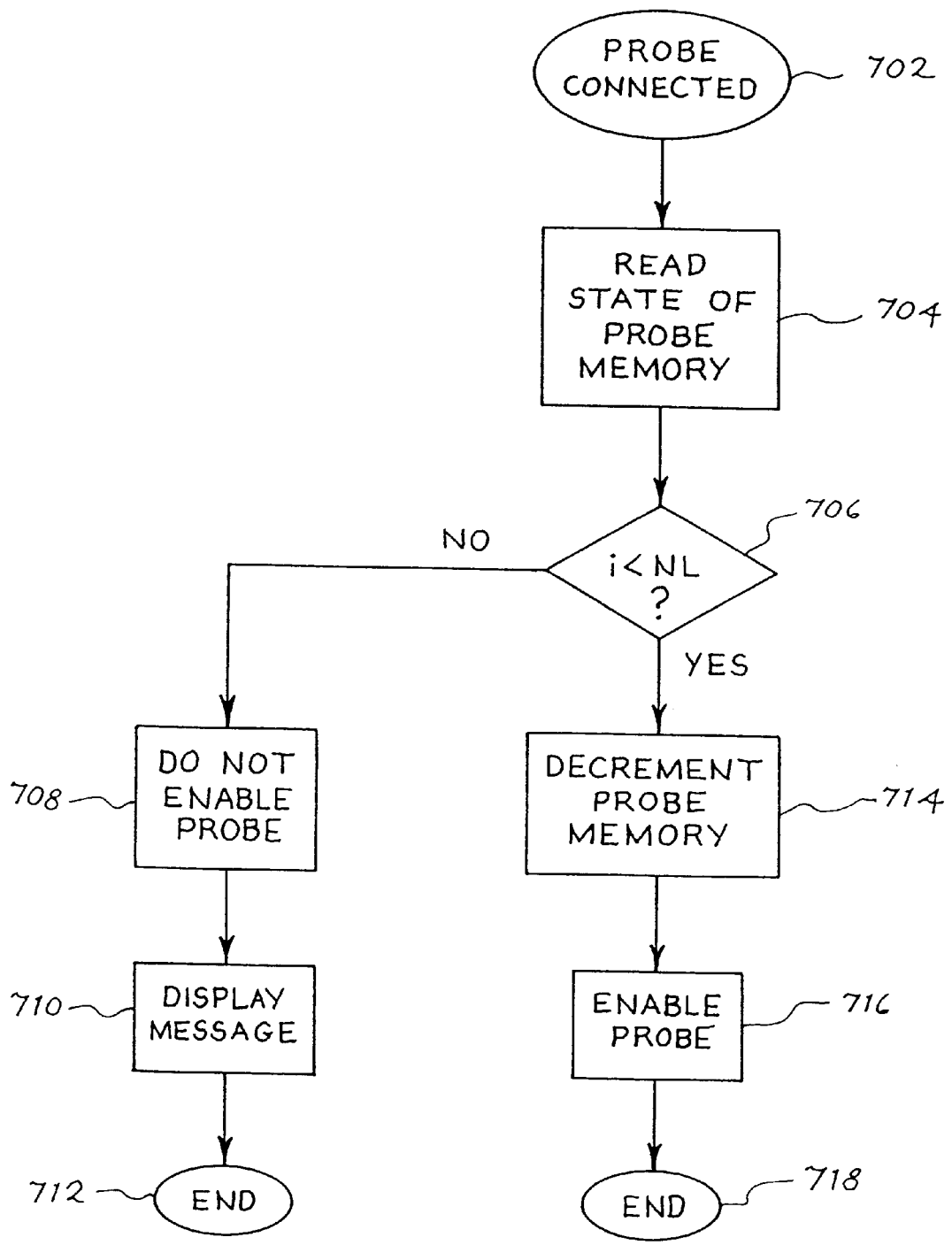
FIG. 7 is a flow chart illustrating an approach for using another embodiment of the invention with non-volatile digital memory.

FIG. 7 is a flow chart illustrating a method for using another embodiment of the invention with non-volatile digital memory. Step 702 involves connecting an ultrasound probe to an ultrasound system. Step 704 involves a processor executing a program in the ultrasound system to read the non-volatile digital memory in the ultrasound probe. Step 706 involves determining whether the ultrasound probe can be used again. If the non-volatile digital memory in the ultrasound probe indicates the maximum amount of ultrasound probe usage has been already reached, then step 708 follows step 706. Step 708 involves disabling the ultrasound probe. Step 710 involves the communication of a message to the user that the ultrasound probe is not available. Step 712 involves ending the ultrasound probe initialization phase of the ultrasound system. If the non-volatile digital memory in the ultrasound probe indicates the maximum amount of ultrasound probe usage has not been already reached, then step 714 follows step 706. Step 714 involves decrementing the non-volatile digital memory in the ultrasound probe. Step 716 involves enabling the ultrasound probe. Step 718 involves the communication of a message to the user that the ultrasound probe is available and ends the ultrasound probe initialization phase of the ultrasound system.

Figure 8:
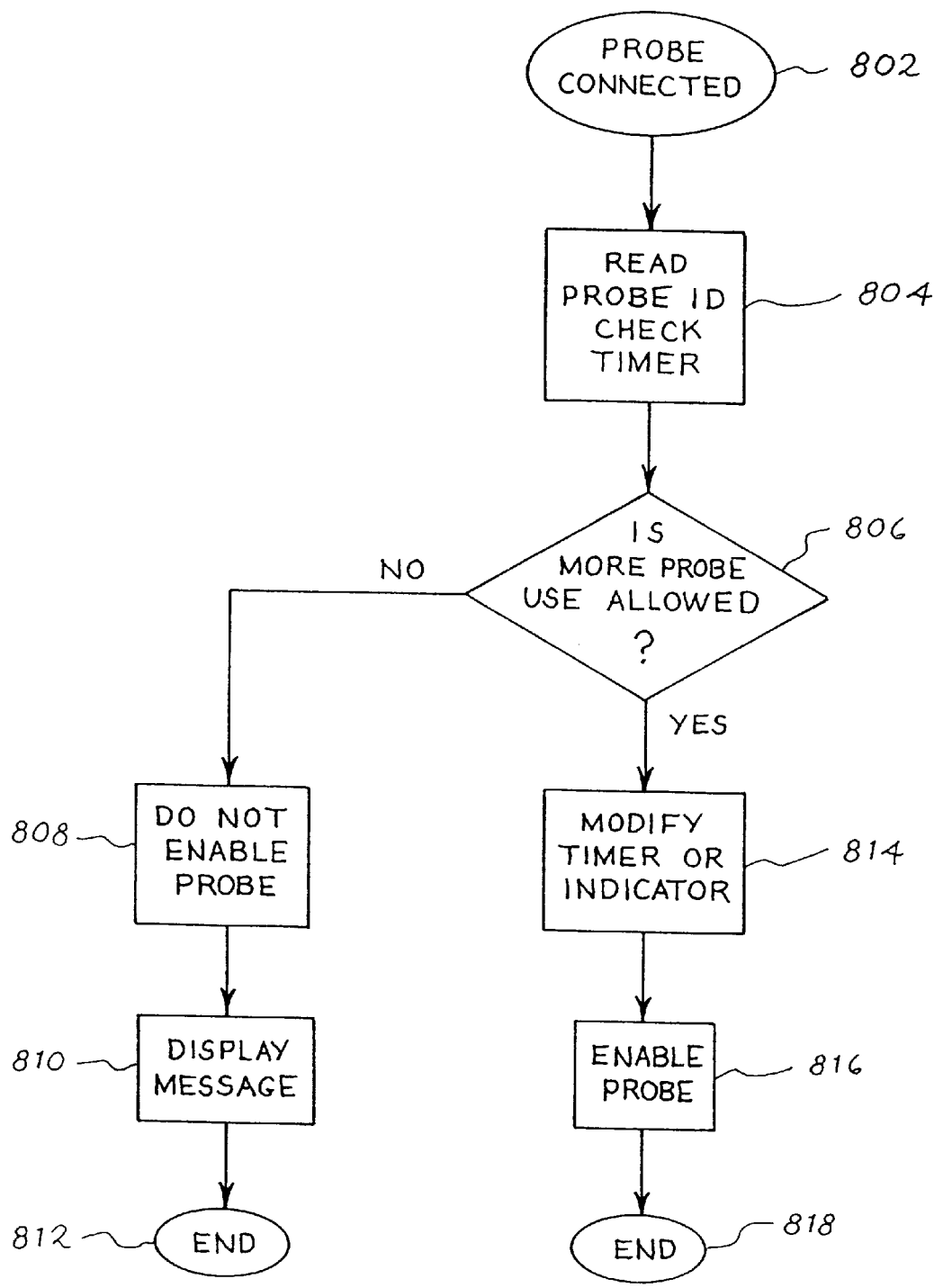
FIG. 8 is a flow chart illustrating an approach for using another embodiment of the invention without memory or fuses.

FIG. 8 is a flow chart illustrating a method for using another embodiment of the invention without memory or fuses. Step 802 involves connecting an ultrasound probe to an ultrasound system. Step 804 involves a processor executing a program in the ultrasound system to read the identification number of the ultrasound probe and check an associated timer or other use indicator assigned to the ultrasound probe inside the ultrasound system. Step 806 involves determining whether the ultrasound probe can be used again. If a timer or other use indicator in the ultrasound system memory indicates the maximum amount of ultrasound probe usage has been already reached, then step 808 follows step 806. Step 808 involves disabling the ultrasound probe. Step 810 involves the communication of a message to the user that the ultrasound probe is not available. Step 812 involves ending the ultrasound probe initialization phase of the ultrasound system. If a timer or other use indicator in the ultrasound memory indicates the maximum amount of ultrasound probe usage has not been already reached, then step 814 follows step 806. Step 814 involves modifying the timer or other use indicator in the ultrasound system. Step 816 involves enabling the ultrasound probe. Step 818 involves the communication of a message to the user that the ultrasound probe is available and ends the ultrasound probe initialization phase of the ultrasound system.

A preferred embodiment of the invention can be used with a medical ultrasound system (e.g., an Acuson Sequoia® ultrasound system or an Acuson Aspen™ ultrasound system). In a preferred embodiment, the entire ultrasound probe diameter can be 5 to 15 mm. For minimally invasive surgery, the entire ultrasound probe diameter is less than 10 mm and the length of the ultrasound probe is between 15 to 30 centimeters (cm).

In the most preferred embodiment of the invention, if the ultrasound probe is re-usable, a plastic sheath is used which is tolerant of at least one application of chemical sterilization, steam sterilization (autoclaving), or Steris sterilization. Plastics that can be used for these embodiments include: Pellethane® thermoplastic polyurethane elastomer available from Dow Corporation, located in Midland, Mich., and Hytrel® polyester elastomer, available from Du Pont Corporation, located in Wilmington, Del.

Ultrasound probes incorporating an embodiment of the invention have significant advantages. The invention enables a more cost effective ultrasound probe design, because a disposable ultrasound probe does not need to be constructed more ruggedly for safe re-use, since it can be reasonably insured that the ultrasound probe will be used only once or a limited number of times. The invention increases patient safety by reducing the risk from a foreseeable misuse of the ultrasound probe.

The exemplary embodiments described herein are for purposes of illustration and are not intended to be limiting. Examples of variations within the scope of this invention include, but are not limited to, the following:

Other types of resistor/fuse arrangements could be used to achieve the same purpose.

Different circuit configurations can be implemented, using other types of electrical elements, e.g., diodes, silicon controlled rectifiers (SCRs), programmable read only memory (PROM), programmable logic arrays (PLAs), and programmable array logic (PAL).

Alternative embodiments of the invention could be implemented with different types of encoders and decoders for the ID programming and ultrasound probe usage control.

Alternative embodiments of the invention could be implemented primarily in software for ID checking and use control.

Alternative embodiments of the invention could be implemented primarily in hardware for ID checking and use control.

Circuitry preferably located in the medical ultrasound system could be located in the ultrasound probe.

Information informing the user of the ultrasound probe status can be presented by using an icon, symbol, alphanumeric character, or graphical display.

Therefore, those skilled in the art will recognize that other embodiments could be practiced without departing from the scope and spirit of the claims set forth below.

What is claimed is:

1. An ultrasound probe, comprising:

a housing, said housing including:
 an ultrasound transducer; and
 a circuit having a plurality of states to limit the use of the ultrasound probe; and wherein the circuit comprises an element that disables the probe as a function of said plurality of states.

2. The ultrasound probe of claim 1 wherein said housing further comprises a programmable memory that indicates the ultrasound probe is inoperable.

3. The ultrasound probe of claim 1, wherein said plurality of states further includes a state that indicates the ultrasound probe is inoperable.

4. The ultrasound probe of claim 1, wherein the circuit includes a plurality of fuses.

5. The ultrasound probe of claim 1, wherein the circuit causes a thermal fault to prevent further use of the ultrasound probe.

6. The ultrasound probe of claim 1, wherein said circuit operates independently of an ultrasound system coupled with said ultrasound probe.

7. An ultrasound probe, comprising:

an ultrasound transducer; and a circuit having at least one discrete state to limit the use of the ultrasound probe to a fixed number of uses, wherein each of said at least one discrete state represents one of said fixed number of uses; and wherein expiration of all of said at least one discrete state renders said ultrasound probe unusable.

8. The ultrasound probe of claim 7, further comprising means for expiring one of said at least one discrete state.

9. The ultrasound probe of claim 7, wherein the circuit includes at least one fuse.

10. The ultrasound probe of claim 9, wherein one of the at least one fuse is permanently open-circuited upon each power-on of the ultrasound probe.

11. The ultrasound probe of claim 7, wherein the circuit comprises an element that disables the probe after one use.

12. An ultrasound probe, comprising:

an ultrasound transducer; and a circuit having at least one discrete state to limit the use of the ultrasound probe to a fixed number of uses, wherein each of said at least one discrete state represents one of said fixed number of uses; and wherein expiration of all of said at least one discrete state causes said ultrasound probe to indicate a thermal fault to an ultrasound system coupled with said ultrasound probe.

13. The ultrasound probe of claim 12, further comprising means for expiring one of said at least one discrete state.

14. The ultrasound probe of claim 12, wherein the circuit includes at least one fuse.

15. The ultrasound probe of claim 14, wherein one of the at least one fuse is permanently open-circuited upon each power-on of the ultrasound probe.

16. The ultrasound probe of claim 12, wherein the circuit comprises an clement that disables the probe after one use.

17. A method of limiting the use of an ultrasound probe comprising:
   (a) providing a circuit with at least one discrete state within said ultrasound probe representing one of a fixed number of uses of said ultrasound probe;
   (b) expiring one of said at least one discrete state upon power on of said ultrasound probe;
   (c) allowing use of said ultrasound probe, by said circuit, when at least one of said at least one discrete state remains unexpired; and
   (d) preventing use of said ultrasound probe, by said circuit, when all of said at least one discrete state are expired.

18. The method of claim 17 further comprising:
   (e) simulating a thermal fault within said ultrasound probe, by said circuit, when all of said at least one discrete state are expired.

19. The method of claim 17 wherein said at least one discrete state comprises at least one fuse, the method further comprising
   (e) open circuiting, permanently, said at least one fuse upon power on of said ultrasound probe.

* * * * *